Figure 1:
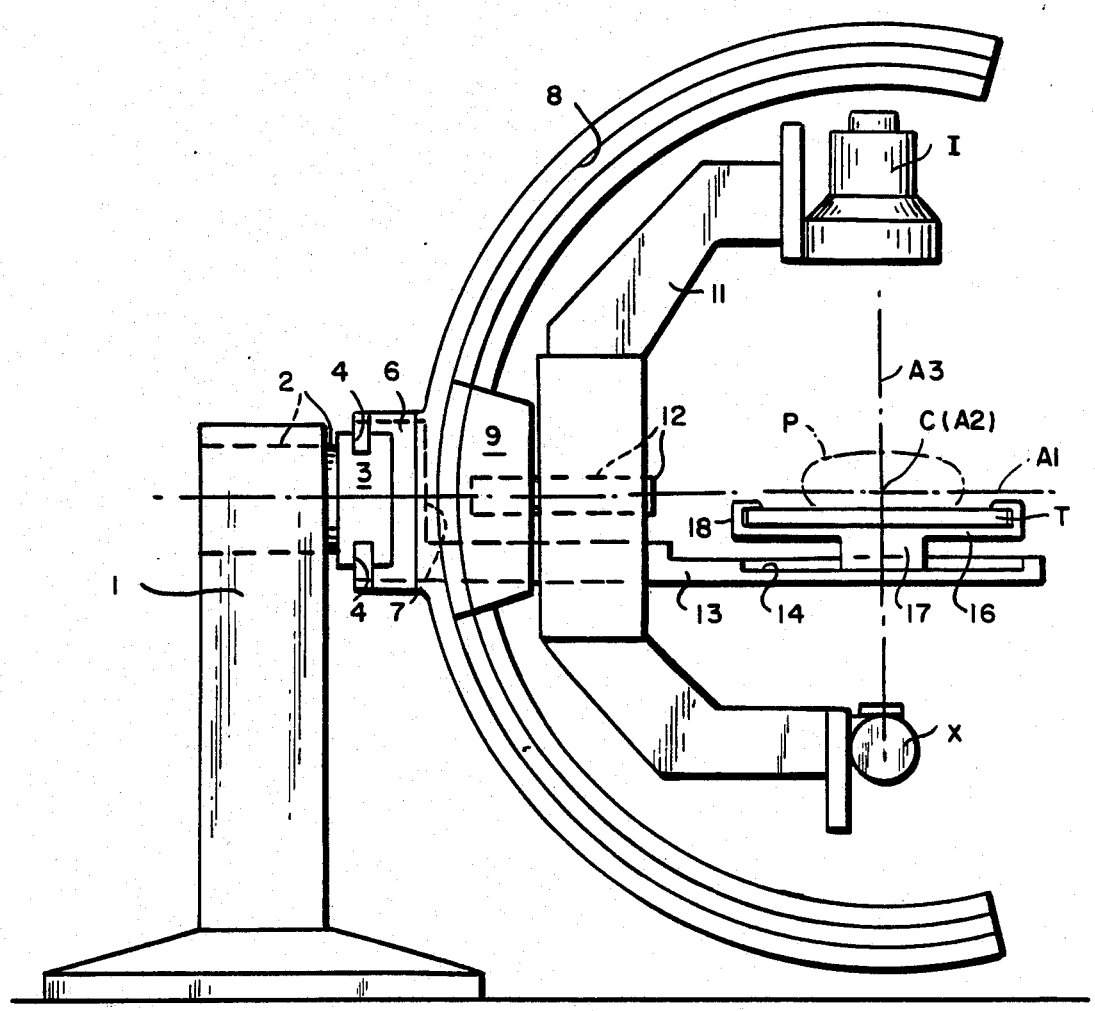

United States Patent [19]

Rossi

[11] Patent Number: 4,653,083
[45] Date of Patent: Mar. 24, 1987

[54] SPHERICAL X-RAY ANGULATION AND PATIENT TILTING SYSTEM

[75] Inventor: Remo J. Rossi, Billerica, Mass.
[73] Assignee: John K. Grady, Littleton, Mass.
[21] Appl. No.: 710,437
[22] Filed: Mar. 11, 1985
[51] Int. Cl.[4] .............................................. H05G 1/02
[52] U.S. Cl. .................................... 378/196; 378/195; 378/197; 378/208; 378/209
[58] Field of Search ........................ 378/11, 15, 17, 20, 378/38–40, 176–179, 189, 190, 193, 195–197, 208, 209

[56] References Cited

U.S. PATENT DOCUMENTS

| 3,281,598 | 10/1966 | Hollstein | 378/179 |
| 3,617,749 | 11/1971 | Massiot | 378/189 |
| 4,503,552 | 3/1985 | Miyahara et al. | 378/196 |

FOREIGN PATENT DOCUMENTS 2238706 2/1974 Fed. Rep. of Germany ...... 378/196

Primary Examiner—Craig E. Church
Assistant Examiner—John C. Freeman
Attorney, Agent, or Firm—James H. Grover

[57] ABSTRACT

An X-ray system has radiation carriage for an X-ray source and receptor and a table carriage for a patient. The radiation carriage moves along a circular track on a primary carriage which in turn is on a beam rotating on a standard so that a patient at the isocenter of the two circular movements can be X-rayed at adjusted angles from spherical loci. The beam also pivotally supports a table carriage so that as the patient is inclined with the table the adjusted angle of the radiation is maintained.

4 Claims, 2 Drawing Figures

SPHERICAL X-RAY ANGULATION AND PATIENT TILTING SYSTEM

BACKGROUND OF THE INVENTION

Many X-ray procedures require that the patient be moved from a horizontal resting position on an X-ray table toward an upright position to improve the radiological visibility of internal organs, increase the gravity effect on radio-opaque dye circulation, or to aid breathing, as examples. Upright inclination may be desirable only during brief radiographic exposure periods, and adjustment of the X-ray tube and its associated receptor with their radiation axis centered on a selected organ of the patient is preferably made before patient inclination and exposure. After inclination a program of several exposures at various fixed angulations of the radiation axis may be made.

It is an object of the present invention to provide an X-ray system which will allow fixing the angulation of the radiation axis between an X-ray source and receptor while a patient is in a comfortable horizontal position which maintains the fixed angulation while the patient is inclined to a more erect position, and which further allows spherical angulation of the radiation axis after inclination without changing the centering of the radiation axis on the selected organ. Spherical angulation means direction of X-radiation of an X-ray source tube from any loci on a sphere centered on the patient and an isocenter of the X-ray system. The isocenter is at the intersection of the radiation axis between the radiation source and receptor and the axis of angulation.

SUMMARY OF THE INVENTION

According to the invention an X-ray system for examination of a patient comprises a standard, a beam pivotted on the standard to rotate about a first axis through the standard; a primary carriage on the beam having a circular track centered on a second axis normal to the first axis; a radiation carriage supporting X-radiation source means and a radiation receptor means on a radiation axis intersecting an isocenter on the first and second axes, the radiation carriage being circularly moveable along the track about the second axis for angulation of the radiation axis with respect to the isocenter; and a table carriage on the beam supporting a patient table adjacent the isocenter along the second axis for inclination by pivotting of the beam about the first axis and isocenter from a horizontal position toward an upright position, whereby the primary and radiation carriages are inclined together with the beam and table carriage to maintain the angulation of the radiation axis with respect to the patient as the patient is inclined.

Preferably the radiation carriage is rotatable with respect to the primary carriage about a radius to the track independently of beam rotation, circular movement along the track and rotation of the radiation carriage producing spherical angulation of the radiation axis a selected position relative to the isocenter and patient, the selected angulation position being maintained during patient inclination.

DRAWINGS

Figure 2:
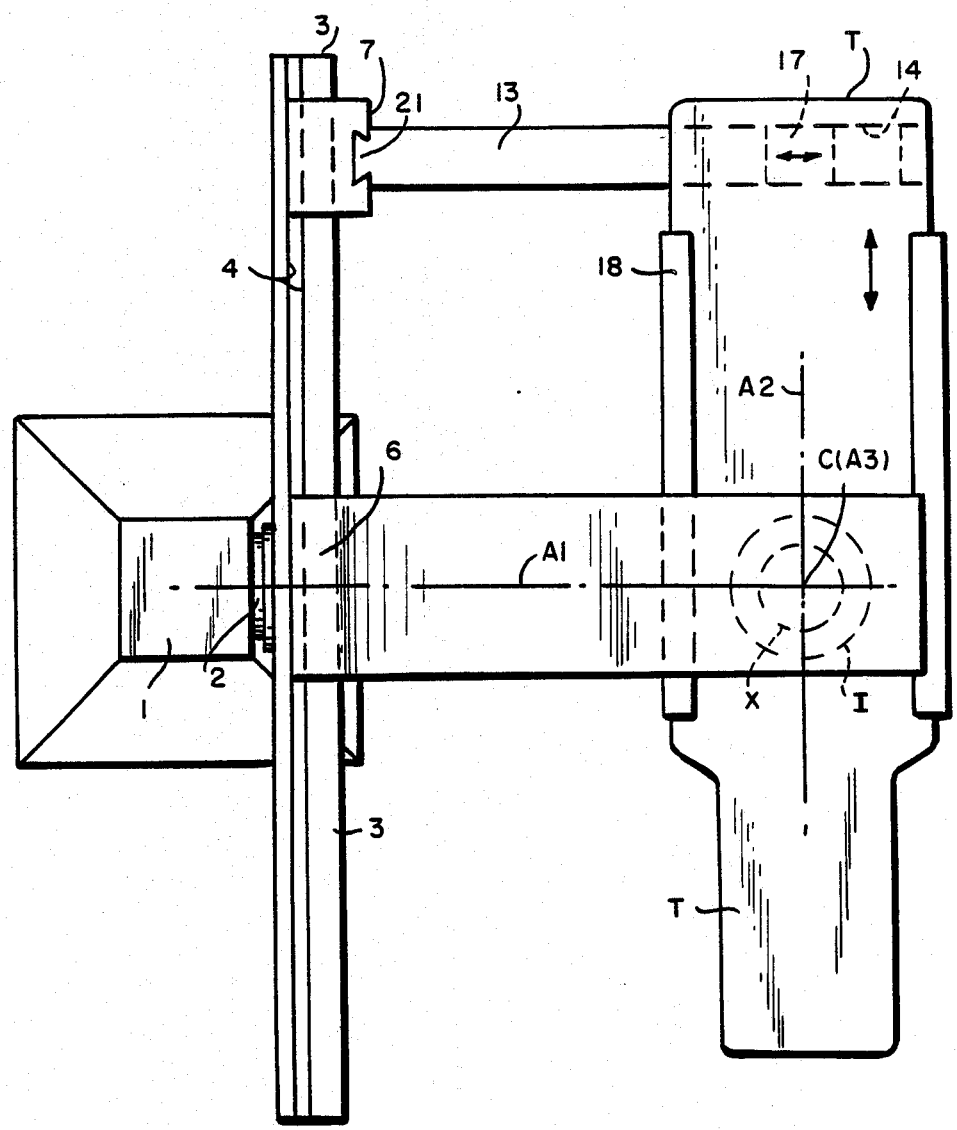

FIG. 1 is an end elevation of an X-ray system with an inclining patient table according to the invention; and
FIG. 2 is a plan view of the system.

DESCRIPTION

The X-ray system of FIGS. 1 and 2 is based on a floor standard 1 through which a shaft 2 extends on a horizontal axis A1. An elongate beam 3 rotating about the shaft 2 axis A1 has a longitudinal, linear track 4 in which a primary carriage 6 and a carriage 7 for a patient table T are slidably supported for independent movement lengthwise of the beam. The primary carriage 6 includes a circular track 8 centered on a second axis A2 and an isocenter C at the intersection of the first and second axes A1 and A2. A radiation carriage 9 is circularly moveable along the circular track 8 about the isocenter. The radiation carriage includes a two-armed support 11 carrying an X-radiation source such as an X-ray tube X on one arm and an X-radiation receptor such as an image intensifier I on the other arm. The radiation source and receptor are aligned on a radiation axis A3 passing through the isocenter C. The two-armed support 11 is rotatably attached to the radiation carriage 9 by a shaft 12 whose axis coincides with the rotational axis A1 of the beam. The combined angulation movement of the radiation carriage 9 along the circular track 8 and rotation of the two-armed radiation support on the shaft 12 (which may be termed spherical angulation) enables a patient P on the table T adjacent the isocenter C to be examined radiologically along most, if not all, radii from an imaginary sphere inwardly to the isocenter.

X-ray apparatus for spherical angulation has been previously described in U.S. Pat. No. 3,892,967, for example, in association with a patient table on the floor of an X-ray room. And inclination of a patient for radiological examination in an upright position has been practiced for many years. But according to the present invention the rotating beam 3 which carries the spherical examination system also carries the patient carriage 7 and table T.

The table carriage 7, like the primary carriage 6, slides on the linear track 4 of the beam 3. Part of the table carriage is an arm 13 extending under the table and having a track 14 parallel to the beam rotational axis A1. A cradle 16 has a foot 17 sliding in the track 14 transversely of the radiation axis A3 for lateral adjustment of a patient. The cradle has two edge guides 18 in which the table T slides longitudinally for head to toe adjustment of the patient. A sliding connection between the table arm and carriage, represented by a dovetail 21, allows movement of the patient table at right angles to its plane and along the radiation axis A3.

All of the linear adjustments of the patient P in the table T are customarily done before the radiation exposure program to select the organ or system to be examined. Also it is usually necessary to angulate the radiation axis before radiological examination. Hitherto the patient has been in the desired inclined position for uncomfortable periods during the adjustments preparatory to examination. But in the present system the adjustments can be made with the patient in a horizontal position which is comfortable and unstressful and sometimes necessary for preliminary dye injection. The patient can then be inclined quickly toward an upright position by rotation of the beam 3 which maintains the selected relation of the radiation axis A3 of the radiation carriage 9 and the patient on the table carriage 7.

It should be understood that the present disclosure is for the purpose of illustration only and that this invention includes all modifications and equivalents which fall within the scope of the appended claims. For example, all the described linear and rotational movements described are customarily effected by motors and manual or programmed computer controls.

I claim:

1. An X-ray system for examination of a patient comprising:

a standard;

a beam pivoted on the standard to rotate about a first axis through the standard;

a primary carriage on the beam having a circular track centered on a second axis normal to the first axis;

a radiation carriage supporting X-radiation source means and a radiation receptor means on a radiation axis intersecting an isocenter on the first and second axes, the radiation carriage being circularly movable along the track about the second axis for angulation of the radiation axis with respect to the isocenter; and a table carriage on the beam supporting a patient table adjacent the isocenter along the second axis for inclination by pivoting of the beam about the first axis and isocenter from a horizontal position toward an upright position wherein the primary carriage is mounted to slide on the beam parallel to the second axis to translate the radiation axis along the patient table, so that the primary and radiation carriages are inclined together with the mean and table carriage to maintain the angulation of the radiation axis with respect to the patient as the patient is inclined.

2. A system according to claim 1 wherein the radiation carriage is rotatable with respect to the primary carriage about a radius to the track independently of beam rotation, circular movement along the track and rotation of the radiation carriage producing spherical angulation of the radiation axis a selected position relative to the isocenter and patient, the selected angulation position being maintained during patient inclination.

3. A system according to claim 2 wherein the radiation carriage includes a two-armed support carrying the radiation source and receptor means on its respective arms.

4. A system according to claim 1 wherein the table carriage is slideable on the beam parallel to the second axis to adjusted positions intersected by the radiation axis.

* * * * *

UNITED STATES PATENT AND TRADEMARK OFFICE
CERTIFICATE OF CORRECTION

PATENT NO. : 4,653,083
DATED : March 24, 1987
INVENTOR(S) : Remo J. Rossi

It is certified that error appears in the above-identified patent and that said Letters Patent are hereby corrected as shown below:

In Claim 1, column 4, line 7, change "mean' to --beam--.

Signed and Sealed this

Twenty-sixth Day of April, 1988

Attest:

DONALD J. QUIGG

Attesting Officer

Commissioner of Patents and Trademarks